US00PP28072P2

(12) United States Plant Patent
Probst

(10) Patent No.: US PP28,072 P2
(45) Date of Patent: May 30, 2017

(54) ***COREOPSIS* PLANT NAMED 'CHARLIZE'**

(50) Latin Name: ***Coreopsis* hybrid**
Varietal Denomination: Charlize

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 18 days.

(21) Appl. No.: 14/756,586

(22) Filed: Sep. 21, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

American Nurseryman Dec. 2014 retrieved on Nov. 22, 2016, retrieved from the Internet at <http://www.amerinursery.com/content/AN/pdf/2015_AN_NewPlants.pdf> pp. 4 and 13-14.*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Charlize' characterized by its compact plant habit reaching an average of 40 cm in height and 65 cm in width, its near sterility, its floriferous and long bloom season that does not require deadheading with bloom commences in late June and lasting until frost in Kensington, Conn., its medium sized inflorescences with fully double ray florets that are light yellow in color, its lack of requirement for vernalization to initiate flowering, its cold hardiness to at least U.S.D.A. Zone 5 and its resistance to powdery mildew and leaf spot.

2 Drawing Sheets

Botanical classification: *Coreopsis* hybrid.
Variety denomination: 'Charlize'.

BACKGROUND OF THE INVENTION

The present invention relates to a new and distinct cultivar of a plant botanically of hybrid origin and known as *Coreopsis*. The new cultivar will be referred to hereafter by its cultivar name 'Charlize'. 'Charlize' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and are cold hardy at least to U.S.D.A. Zone 5 in a wide range of flower colors and plant forms on plants that do not require vernalization to initiate flowering.

The Inventor made a controlled cross in June of 2010 in his test garden in Hubbardston, Mass. between an unnamed proprietary plant from the Inventor's breeding program, reference no. G 08-2 (not patented), as the female parent and pollen that was pooled from a variety of unnamed, relatively sterile, proprietary plants (not patented) from his breeding program as the male parent. The exact male parentage is therefore unknown. 'Charlize' was selected in September of 2011 as a single unique plant amongst the resulting seedlings.

Asexual propagation of the new cultivar was first accomplished by stem cuttings in Kensington, Conn. in September of 2011 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Charlize' as unique cultivar of *Coreopsis*.

1. 'Charlize' exhibits a compact plant habit reaching an average of 40 cm in height and 65 cm in width.
2. 'Charlize' is nearly sterile and exhibits a floriferous and long bloom season that does not require deadheading; blooming commences in late June and lasts until frost in Kensington, Conn.
3. 'Charlize' exhibits medium sized inflorescences with fully double ray florets that are light yellow in color.
4. 'Charlize' does not require vernalization to initiate flowering.
5. 'Charlize' exhibits cold hardiness to at least U.S.D.A. Zone 5.
6. 'Charlize' exhibits resistance to powdery mildew and leaf spot.

The female parent of 'Charlize', G 08-2, differs from 'Charlize' in being very fertile. 'Charlize' can be compared to the *Coreopsis* cultivars 'Sundancer' (U.S. Plant Pat. No. 7,823) and 'Galaxy' (U.S. Plant Pat. No. 21,999). 'Sundancer' is similar to 'Charlize' in having a compact plant habit, in having inflorescences with double ray florets and in being relatively sterile. 'Sundancer' differs from 'Charlize' in having inflorescences that are gold in color. 'Galaxy' is similar to 'Charlize' in having inflorescences with extra ray florets that are light yellow in color, in having a compact plant habit, in having resistance to powdery mildew, in being hardy to at least U.S.D.A. Zone 5 and in not requiring vernalization to initiate flowering. 'Galaxy' differs from 'Charlize' in having semi-double inflorescences instead of near fully double, in having a more narrow plant growth width throughout the growing season and in producing fewer inflorescences over the span of the blooming season.

BRIEF DESCRIPTION OF THE DRAWINGS

The accompanying colored photographs illustrate the overall appearance and distinct characteristics of the new *Coreopsis*.

The photograph in FIG. 1 was taken of a three month-old plant of 'Charlize' as grown outdoors in a 1.5-liter container from a 128-cell plug in Hillegom, The Netherlands and provides a side view of a plant in bloom.

Figure 1:
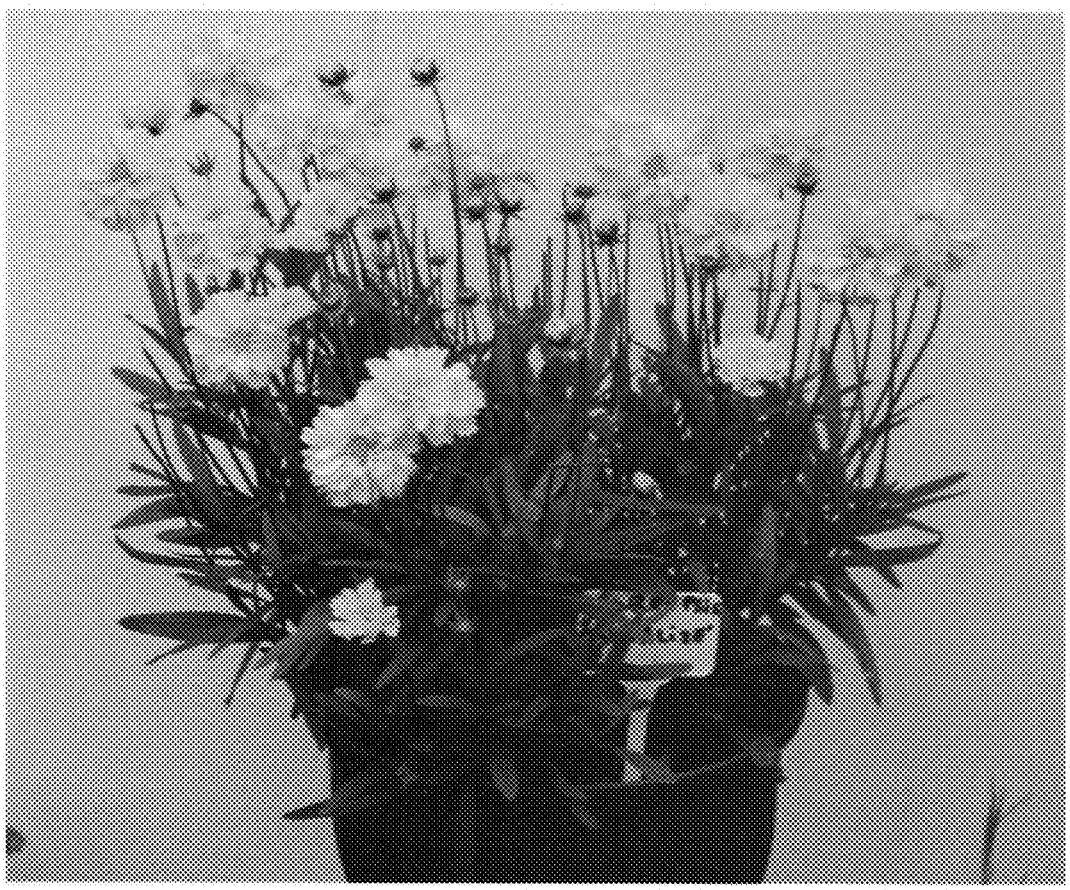
Figure 2:
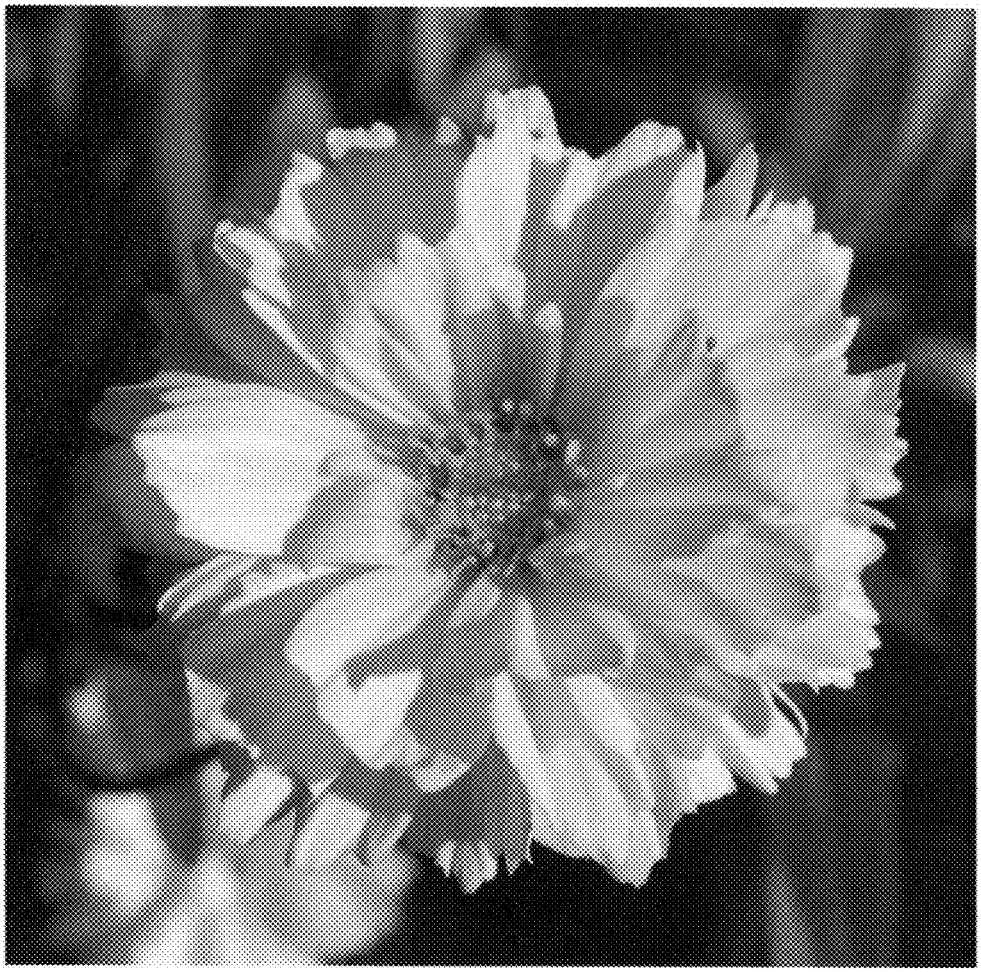

The photograph in FIG. 2 was taken of 4 month-old plant of 'Charlize' as grown in the ground in New Braintree, Mass. and provides a close-up view of an inflorescence.

The colors in the photograph may differ slightly from the color values cited in the detailed botanical description, which accurately describe the colors of the new *Coreopsis*.

DETAILED BOTANICAL DESCRIPTION

The following is a detailed description of three month-old plants of the new cultivar as grown outdoors in one-gallon containers from 128-cell plugs in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from late June until frost in Kensington, Conn.

*Plant type*.—Herbaceous perennial.

*Plant habit*.—Clump-forming, compact.

*Height and spread*.—An average of 40 cm in height and 65 cm in width in the landscape.

*Cold hardiness*.—At least in U.S.D.A Zone 5.

*Diseases resistance*.—Has been observed to be resistant to powdery mildew (*Podosphaera macularis*) and leaf spot (*Pseudomonas cichorii*).

*Root description*.—Fibrous when young, becoming fleshy with age, 162C in color.

*Root development*.—Roots initiate in 6 to 8 days and fully develop in a 128-cell plug in about 28 days with bottom heat and rooting hormone at optimal times of the year.

*Propagation*.—Division and stem cuttings (preferred).

*Growth rate*.—Moderately vigorous, but stays compact.

Stem description:

*Shape*.—Oval, ridged.

*Stem color*.—144A to 144B.

*Stem size*.—Main and secondary stems; an average of 17 cm in length and 2.5 mm in width.

*Stem surface*.—Glabrous.

*Stem aspect*.—Upright.

*Branching habit*.—Well-branched, an average of 5 main branches, 3 secondary branches per main stem.

*Internode length*.—An average of 3.2 cm.

Foliage description:

*Leaf division*.—Simple.

*Leaf margins*.—Entire to trifid and moderately pubescent.

*Leaf size*.—Variable, up to 9.5 cm in length and 1.1 cm in width when entire, up to 9.2 cm in length and 4.9 cm in width when trifid.

*Leaf shape*.—Oblanceolate when entire, oblanceolate lobes when trifid.

*Leaf base*.—Clasping.

*Leaf apex*.—Acute.

*Leaf venation*.—Pinnate to reticulate, inconspicuous, matches leaf color on upper and lower surface.

*Leaf attachment*.—Sessile.

*Leaf arrangement*.—Opposite.

*Leaf number*.—An average of 10 (5 pairs).

*Leaf surface*.—Upper and lower surface glabrous.

*Leaf color*.—Upper surface 137B and lower surface 144A.

Inflorescence description:

*Inflorescence type*.—Composite with a three rows of overlapping ray florets surrounding disk florets in the center, solitary.

*Lastingness of inflorescence*.—8 to 10 days until senescence of ray flowers, longer in cool temperatures, bracts and disk flowers are persistent.

*Fragrance*.—Moderate grassy scent.

*Quantity of inflorescences*.—An average of 5 per main branch.

*Inflorescence size*.—An average of 1.5 cm in depth and up to 4 cm in diameter.

*Inflorescence buds*.—Average of 6 mm in depth and in diameter, globose in shape, color; a blend of 144A and 153A.

*Peduncle*.—Average of 6 cm in length and 1.2 mm in width, glabrous surface, 144A to 144B in color, strong.

Involucral bracts:

*Bract number*.—8, 4 outer bracts and 4 inner bracts.

*Bract arrangement*.—Bracts surround receptacle in a campanulate form, held close to lower surface of ray florets.

*Bract size*.—An average of 7.5 mm in length and 4 mm in width.

*Bract color*.—Translucent; apex, a blend between 153C with base 144A to 144B and margins 155C.

*Bract texture*.—Outer and inner surface; glabrous and satiny.

*Bract apex*.—Acute.

*Bract base*.—Truncate.

*Bract margins*.—Entire.

*Bract shape*.—Ovate.

Ray florets (sterile):

*Number*.—An average of 24 arranged in three overlapping rows.

*Shape*.—Obovate to ovate.

*Size*.—An average of 1.8 cm in length and 1 cm in width.

*Apex*.—Irregular 3 to 5 lobed.

*Base*.—Cuneate.

*Margins*.—Entire with apex notched.

*Aspect*.—Held outward and upward.

*Texture*.—Glabrous on upper and lower surface.

*Color*.—When opening and when fully open inner and outer surface; a blend of 8A and 13A.

Disk flowers (perfect):

*Shape*.—Tubular, corolla is fused, flared at apex.

*Number*.—About 80.

*Size*.—About 4.5 mm in length and 0.7 mm in width.

*Color*.—En masse; a blend of 13A, corolla tube; 6B in color.

*Receptacle*.—About 3.2 mm in diameter and 1.5 mm in depth, color; 150D, disk-shaped.

Reproductive organs:

*Presence*.—Disk flowers are perfect, ray flowers are sterile.

*Gynoecium*.—1 Pistil, 4.5 mm in length, style is very fine, translucent and 8D in color, stigma is 2-lobed and 13B in color, ovary is about 1 mm in length and width 0.5 mm, inferior, and 193D in color.

*Androcoecium*.—3 stamens, fused into tube surrounding style, 1.5 mm in length and 0.2 mm in width, about 175A in color, anthers not well developed, pollen is low in quantity, an average of 5 petaloids an average of 4 mm in length and 2 mm in width, roughly oblanceolate in shape, color and surface match ray florets.

*Fruit/seed*.—Nearly sterile, no fruit or seed development has been observed to date.

It is claimed:

1. A new and distinct cultivar of *Coreopsis* plant named 'Charlize' as herein illustrated and described.

* * * * *